United States Patent [19]

Royster et al.

[11] Patent Number: 4,995,067

[45] Date of Patent: Feb. 19, 1991

[54] SURGICAL AND X-RAY OPERATION TABLE EXTENSION

[75] Inventors: Robert M. Royster, Social Circle, Ga.; Tracy A. Gordon, San Antonio, Tex.

[73] Assignee: The United States of America as represented by the Secretary of the Air Force, Washington, D.C.

[21] Appl. No.: 417,533

[22] Filed: Oct. 5, 1989

[51] Int. Cl.$^5$ .................... G03B 42/02; A61B 6/04; A47C 19/00

[52] U.S. Cl. ................. 378/177; 378/209; 5/60; 5/61; 5/62

[58] Field of Search ............ 378/208, 209, 177, 180; 269/322; 5/60-64

[56] References Cited

U.S. PATENT DOCUMENTS

| D. 287,626 | 1/1987 | Wilson et al. | |
|---|---|---|---|
| 429,716 | 6/1890 | Bishop | 5/61 |
| 1,980,848 | 11/1934 | Cass | 378/180 |
| 2,609,261 | 9/1952 | Parker | |
| 2,872,259 | 2/1959 | Thorpe | |
| 3,253,284 | 5/1966 | St. John | 5/62 |
| 4,193,148 | 3/1980 | Rush | 378/177 |
| 4,244,358 | 1/1981 | Pyers | 5/61 |
| 4,584,989 | 4/1986 | Stith | 378/209 |
| 4,602,378 | 7/1986 | Kelman et al. | |
| 4,658,450 | 4/1987 | Thompson | 5/62 |
| 4,700,373 | 10/1987 | Miller | |
| 4,700,938 | 10/1987 | Chambron | 378/209 |

FOREIGN PATENT DOCUMENTS 2413073  8/1979  France .

*Primary Examiner*—Janice A. Howell
*Assistant Examiner*—Kim Kwok Chu
*Attorney, Agent, or Firm*—Bobby D. Scearce; Donald J. Singer

[57] ABSTRACT

An extension for an operating table having an adjustable surface for supporting a patient thereon for surgical procedures is described which comprises an x-ray transparent platform defining an upper surface of sufficient size for supporting a patient thereon, brackets for attachment of a first end of the platform to the operating table, an adjustable support at a second end of the platform for selectively raising and lowering the platform and for selectively tilting the platform about a longitudinal axis thereof in cooperation with position adjustments of the operating table, and a hanger attached to the under surface of the platform for holding x-ray film for use in taking intra-operative x-ray images of the patient.

2 Claims, 1 Drawing Sheet

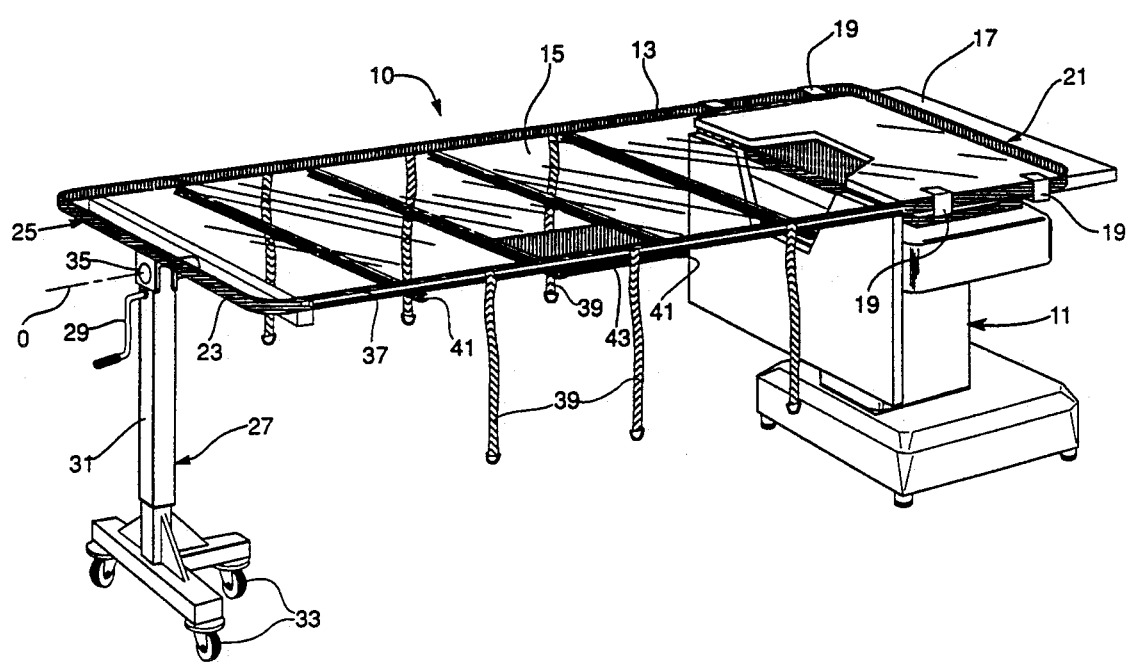

SURGICAL AND X-RAY OPERATION TABLE EXTENSION

RIGHTS OF THE GOVERNMENT

The invention described herein may be manufactured and used by or for the Government of the united States for all governmental purposes without the payment of any royalty.

BACKGROUND OF THE INVENTION

The present invention relates generally to surgical operating tables, and more particularly to a novel extension for an operating table allowing routine intra-operative use of x-rays.

In the course of certain surgical operations, it is highly desirable to have x-ray images of the patient available for guidance to the surgeon in performing the surgery. Use of intra-operative x-rays is particularly desirable in the field of orthopedic surgery. For example, a recently developed spine fixation procedure known as a pedicle screw implantation is a high risk operation and is technically very demanding. Insertion of pedicle screws in the course of the operation under fluoroscopic control is desirable and would substantially reduce the risk associated with the operation.

The invention meets a need in the field of orthopedic surgery as just suggested by providing an attachment or extension to a conventional operating table comprising a fluoroscopy table for supporting the patient during surgery. The invention is attachable to a conventional operating table and movable therewith and comprises an x-ray transparent supporting surface for the patient. Attachment means are provided on the underside of the supporting surface at a location beneath the patient for holding x-ray film cartridges for intra-operative use.

Although the operating table extension of the invention is particularly useful in facilitating insertion of pedicle screws under fluoroscopic control during orthopedic surgery on the spine, the invention may find substantial further use in other orthopedic surgical procedures, such as in intramedullary rodding and fixation of femur and tibia fractures, pelvic surgery, and hip arthroplasty and other hip surgery. All such orthopedic procedures may, with the assistance of the operating table extension described herein, be performed more efficiently and with less morbidity risk than heretofore possible using conventional tables.

It is therefore a principle object of the invention to provide an improved surgical operating table.

It is a further object of the invention to provide a surgical operating table extension having means for intra-operative use of routine x-rays and image intensification.

These and other objects of the invention will become apparent as the detailed description of representative embodiments proceeds.

SUMMARY OF THE INVENTION

In accordance with the foregoing principles and objects of the invention, an extension for an operating table having an adjustable surface for supporting a patient thereon for surgical procedures is described which comprises an x-ray transparent platform defining an upper surface of sufficient size for supporting a patient thereon, brackets for attachment of a first end of the platform to the operating table, an adjustable support at a second end of the platform for selectively raising and lowering the platform and for selectively tilting the platform about a longitudinal axis thereof in cooperation with position adjustments of the operating table, and a hanger attached to the under surface of the platform for holding x-ray film for use in taking intra-operative x-ray images of the patient.

DESCRIPTION OF THE DRAWINGS

The invention will be more clearly understood from the following detailed description of representative embodiments thereof read in conjunction with the accompanying drawing which is a perspective view of the operating table extension of the invention attached to a conventional operating table.

DETAILED DESCRIPTION

Referring now to the drawing, shown therein is a perspective view of the operating table extension 10 of the invention attached to a conventional operating table 11 (such as the Amsco 2080 table manufactured by American Sterilizer Co. of Erie, Pa.). Extension 10 comprises a platform 13 defining a surface 15 of sufficient size (e.g. about 2 feet by 8 feet) for comfortably supporting a patient (not shown) during surgery. Platform 13 comprises a substantially rigid slab 23, 1 to 1½ inches thick of wood, plastic, plexiglass, laminated plywood or other structural material transparent to x-rays. Platform 13 is configured as an extension to an existing table element 17 of operating table 11; according, brackets 19 of appropriate type and number are included on platform 13 for attachment near one end 21 thereof to operating table 11 as suggested in the drawing.

The other end 25 of platform 13 is supported by telescoping leg support assembly 27 providing means for selectively raising and lowering platform 13 in positioning a patient during surgery. Raising and lowering of platform 13 may be facilitated by means represented by crank arm 29 engaging conventional telescoping mechanism included within upright member 31 of assembly 27. Leg support assembly 27 may be supported on a floor surface by a rigid base or tripod or by a plurality of casters 33 as suggested in the drawing. The upper end of leg support assembly 27 includes swivel mount 35 attached to platform 13 for adjustably positioning platform 13 about a longitudinal axis O in cooperation with corresponding adjustment of table element 17 of operating table 11.

On each side of platform 13 is a side rail 37 to facilitate attachment of restraining belts 39 for holding a patient on platform 13 during surgery or for attachment of arm boards (not shown) useful in surgical procedures on the hand or arm. Beneath platform 13 and attached to the underside thereof or to side rails 37 are mounted one or more sets of hangers 41 for slideably receiving x-ray film cartridges 43 for use in taking intra-operative x-ray images of the patient.

In performing a surgical procedure utilizing the operating table extension of the invention, a patient may be restrained on surface 15 of platform 13 using belts 39. Platform 13 may be raised or lowered as needed at leg support assembly 27 in cooperation with operating table 11 and tilted about axis O in order to position the patient suitably for performing the intended surgical procedure. X-ray images may be taken at any time during the surgical procedure by positioning the x-ray unit (not shown) over the patient and exposing the film cartridges 43 through selected parts of the patients's body.

The invention therefore provides an attachment for an operating table allowing routine intra-operative use of x-rays. It is understood that modifications to the invention may be made as might occur to one with skill in the field of the invention within the scope of the claims. All embodiments contemplated hereunder which achieve the objects of the invention have therefore not been shown in complete detail. Other embodiments may be developed without departing from the spirit of the invention or from the scope of the appended claims.

We claim:

1. An extension for an operating table having an adjustable table element defining a surface for supporting a patient for surgical procedures, said extension comprising:

(a) a platform defining an upper surface of sufficient size for supporting a patient thereon, said platform comprising a material transparent to x-rays;

(b) means at a first end of said platform for attachment of said platform to an operating table;

(c) adjustable support means at a second end of said platform for selectively raising and lowering said platform, said support means including swivel means for selectively tilting said platform about a longitudinal axis of said platform in cooperation with position adjustments of the adjustable table element of said operating table; and (d) side rails on each side of said platform and a belt attached to each of said rails for use in restraining said patient during a surgical procedure; and (e) means attached to said platform and mounted on the under surface thereof for holding x-ray film for use in taking intra-operative x-ray images of said patient.

2. The extension of claim 1 wherein said platform comprises a material selected from the group consisting of wood, plastic, plexiglass and laminated plywood.

* * * * *